US012616563B2

(12) United States Patent
Choi

(10) Patent No.: US 12,616,563 B2
(45) Date of Patent: *May 5, 2026

(54) DEVICE FOR MITIGATING URINARY INCONTINENCE POST PROSTATECTOMY

(71) Applicant: LEVEE MEDICAL, INC., Durham, NC (US)

(72) Inventor: Bruce Choi, Durham, NC (US)

(73) Assignee: Levee Medical, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/937,356

(22) Filed: Nov. 5, 2024

(65) Prior Publication Data

US 2025/0064569 A1 Feb. 27, 2025

Related U.S. Application Data

(63) Continuation of application No. 17/012,555, filed on Sep. 4, 2020, now Pat. No. 12,150,849.

(51) Int. Cl.
*A61F 2/00* (2006.01)

(52) U.S. Cl.
CPC ...... *A61F 2/004* (2013.01); *A61F 2210/0014* (2013.01); *A61F 2220/0008* (2013.01); *A61F 2250/0097* (2013.01)

(58) Field of Classification Search
CPC ............. A61B 17/11; A61B 2017/1132; A61F 2/0036; A61F 2/04; A61F 2/042; A61F 2002/047; A61F 2210/0014; A61F 2220/0008; A61F 2230/0067
See application file for complete search history.

(56) References Cited

U.S. PATENT DOCUMENTS

| | | | |
|---|---|---|---|
| 5,925,054 A | | 7/1999 | Taylor et al. |
| 12,150,849 B2 * | | 11/2024 | Choi ...................... A61B 17/11 |
| 12,324,586 B2 | | 6/2025 | Choi |
| 2003/0229364 A1 | | 12/2003 | Seiba |
| 2008/0097584 A1 | | 4/2008 | Inderbitzi |
| 2015/0351767 A1 | | 12/2015 | Zoll et al. |
| 2016/0004283 A1 | | 1/2016 | Ganguly |
| 2016/0174986 A1 | | 6/2016 | Vince et al. |
| 2017/0274123 A1 * | | 9/2017 | Rosell Gratacos ..... C23C 16/06 |
| 2022/0071636 A1 * | | 3/2022 | Choi ...................... A61F 2/0036 |

(Continued)

FOREIGN PATENT DOCUMENTS

| | | |
|---|---|---|
| JP | 2012505698 A | 3/2012 |
| JP | 2023515196 A | 4/2023 |
| WO | 2016004283 A1 | 1/2016 |

OTHER PUBLICATIONS

David D. Childs et al.; "Multimodality Imaging of the Male Urethra: Trauma, Infection, Neoplasm, and Common Surgical Repairs-Special section: Urothelial Disease"; published on-line (Aug. 22, 2019) pp. 3935-3949:vol. 44. No. 12: https://doi.org/10.1007/s00261-019-02127-8; Abdominal Radiology, Springer US, New York.

(Continued)

*Primary Examiner* — Christine H Matthews
(74) *Attorney, Agent, or Firm* — Duane Morris LLP

(57) ABSTRACT

The disclosure relates to apparatus and methods for managing a shape of a junction between a bladder and urethra, for example, to promote urinary continence after a prostatectomy.

25 Claims, 5 Drawing Sheets

(56)　　　　　References Cited

U.S. PATENT DOCUMENTS

2024/0382300 A1　11/2024　Choi

OTHER PUBLICATIONS

S. F. Mungovan et al., Preoperative Membranous Urethral Length Measurement and Continence Recovery Following Radical Prostatectomy: A Systematic Review and Meta-analysis {HHS Public Access, Author manuscript, EUR Urol. J017 Mar. 71(3): pp. 368-378. doi: 10.1016/j.eururo.2016.06.023 {nih.gov)).

V. W. Nitti, MD Rev Urol. 2001; 3{Suppl 1 ): S2-S6. The Prevalence of Urinary Incontinence {nih.gov).

Irwin el. al. BJU Int. Oct. 2011; 108(7): 1132-8 Global Forum on Incontinence, Sweden (2018) Worldwide prevalence estimates of lower urinary tract symptoms, overactive bladder, urinary incontinence and bladder outlet obstruction—Irwin—2011—BJU International—Wiley Online Library.

N. J_ Sathianathen et al., An objective measurement of urinary continence recovery with pelvic floor physiotherapy following robotic assisted radical prostatectomy; Translational Andrology and Urology, vol. 6, Suppl Jul. 2, 2017—(amegroups.com).

K. Hoyland, et al., Post-Radical Prostatectomy Incontinence: Etiology and Prevention, Reviews in Urology_ vol. 16 (4); 2014 https://pmc.ncbi.nlm.nih.gov/articles/PMC4274175/.

W.T. Lowrance et al., Contemporary open and robotic radical prostatectomy practice patterns among urologists in the United States (2012). The Journal of urology, 187(6), 2087-2092.—Abstract—Europe PMC.

B.T. Helfand, et al., Prevalence and Characteristics of Urinary Incontinence in a Treatment-Seeking Male Prospective Cohort—Results from the LURN Study; J Urol. Aug. 2018; 200(2): 397--404. {nih.gov).

B.S. Buckley et al., Prevalence of Urinary Incontinence in Men, Women, and Children—Current Evidence: Findings of the Fourth International Consultation on Incontinence; Urology vol. 76, Issue 2, Aug. 2010, pp. 265-270 https://www.sciencedirecl.com/science/article/pii/S0090429510000191.

S.P. Daugirdas, et al., Urinary Incontnence and Chronic Conditions in the US Population age 50 years and older; In Urogynecol J_ Jan. 3, 2020. doi: 10.1007/s00192-019-04137-y.

Gorina Y, Schappert S, Bercovitz A, et al. Prevalence of incontinence among older Americans. National Center for Health Statistics. Vital Health Stat 3(36). 2014. https://www.cdc.gov/nchs/data/series/sr_03/sr03_036.pdf.

* cited by examiner

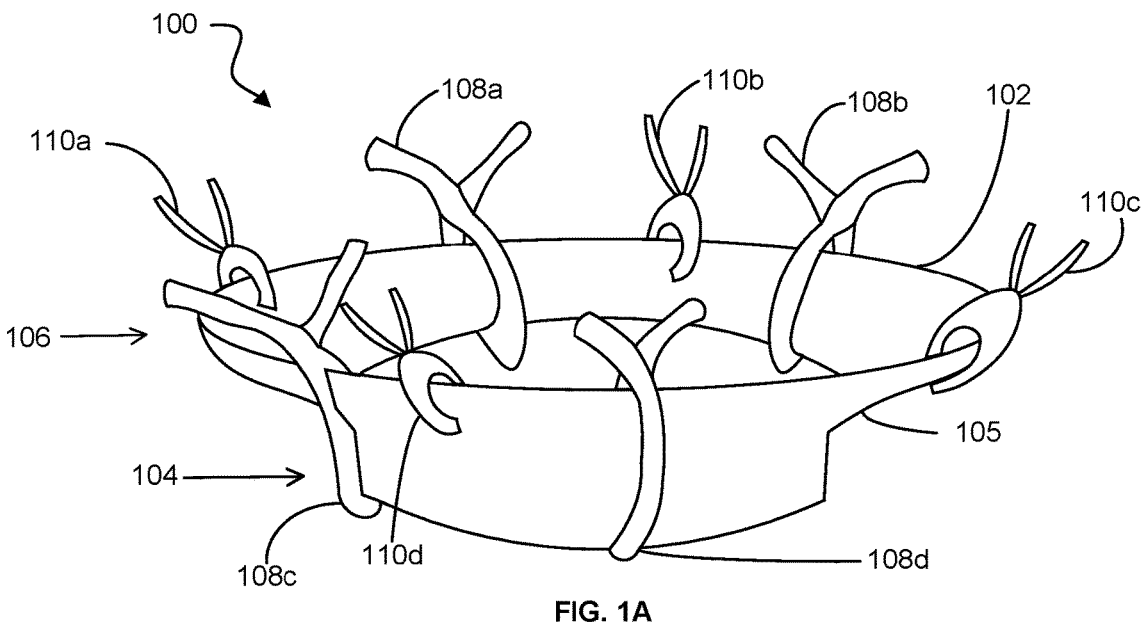
FIG. 1A
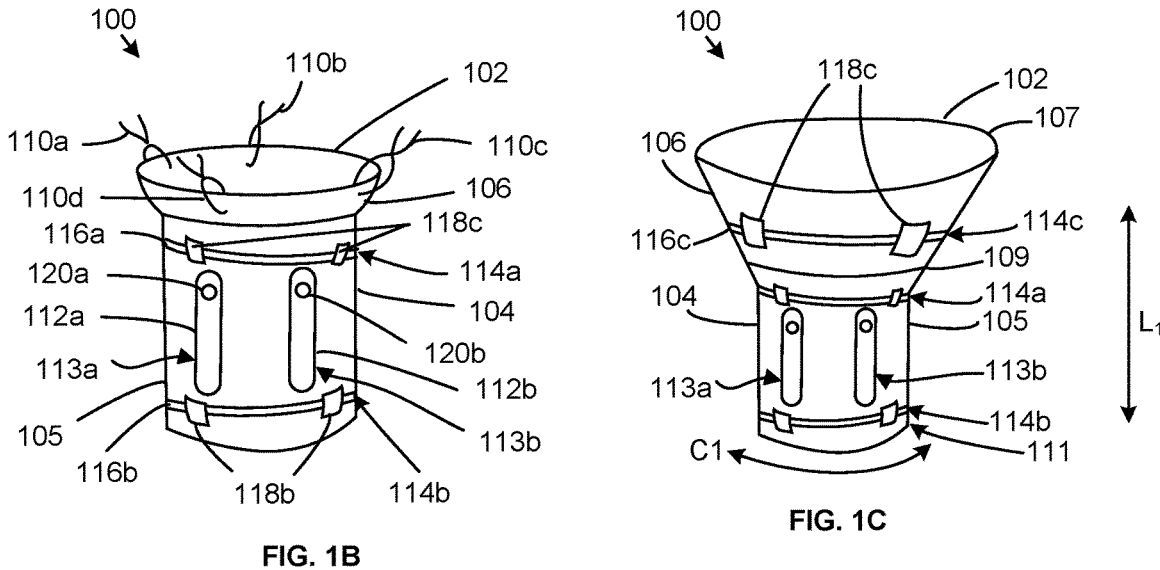
FIG. 1B
FIG. 1C

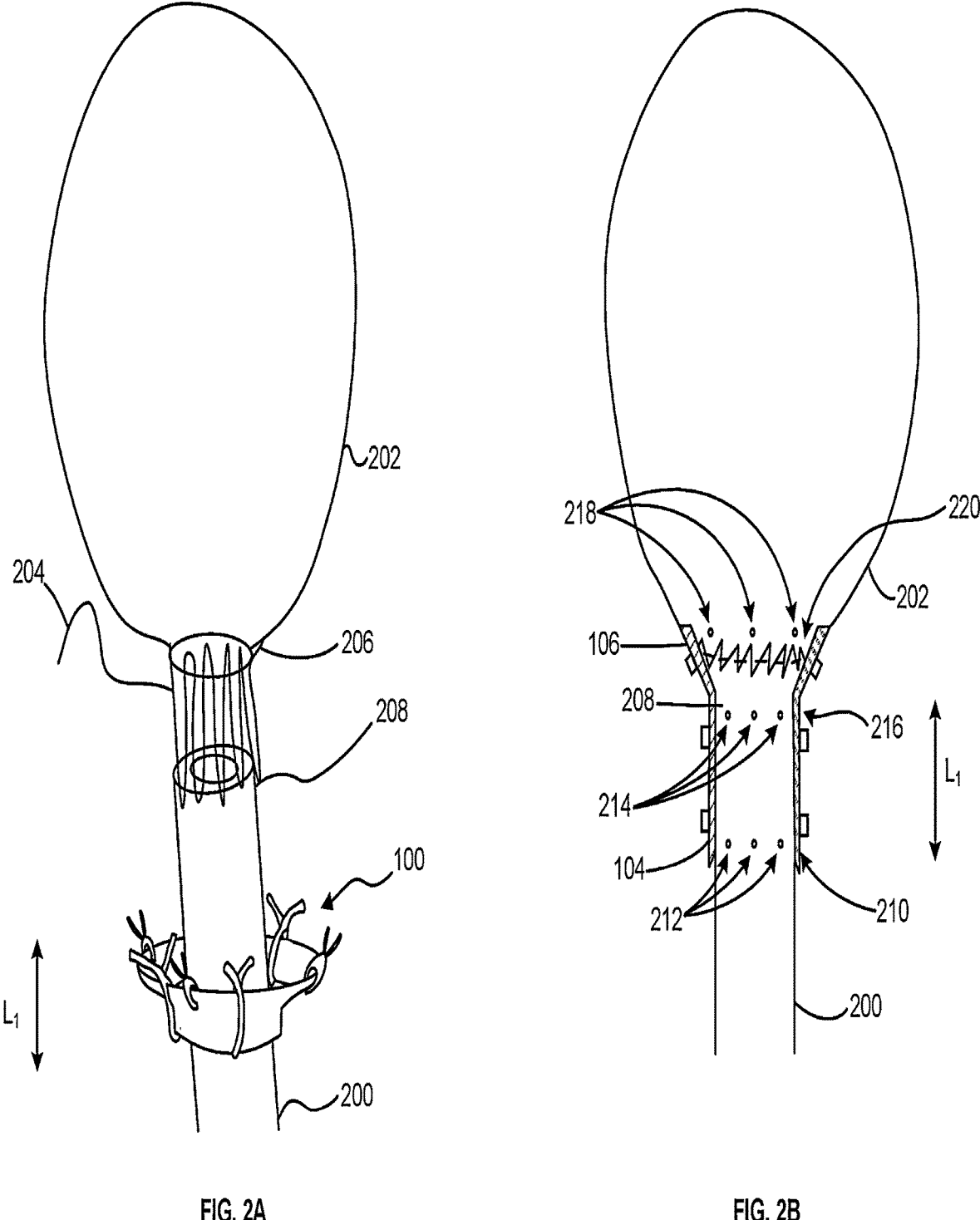
FIG. 2A                    FIG. 2B 113a     113b 102     104

113a     113b

DEVICE FOR MITIGATING URINARY INCONTINENCE POST PROSTATECTOMY

CROSS-REFERENCE TO RELATED APPLICATIONS

This application is a continuation of U.S. patent application Ser. No. 17/012,555, filed 14 Sep. 2020, the entirety of which is hereby incorporated by reference for all purposes as if fully set forth herein.

TECHNICAL FIELD

The present disclosure relates generally apparatus and methods for supporting a connection of a bladder and urethra, and more particularly, to apparatus and methods for managing a shape of a junction between the bladder and the urethra to promote urinary continence after a prostatectomy.

BACKGROUND

Conventional prostatectomy procedures (e.g., radical prostatectomy or simple prostatectomy) remove all or part of the prostate gland, which is positioned at the base of the bladder and around the urethra. These procedures may use various techniques, including a robot-assisted prostatectomy, an open prostatectomy, or a laparoscopic prostatectomy. During the prostatectomy, at least a portion of the prostate gland and at least a portion of the urethra surrounded by the prostate gland is removed from the patient, resulting in the bladder being detached from the remaining portion of the urethra. Subsequent to removing the prostate gland, the bladder is attached to the remaining portion of the urethra. However, as the length of the urethra is now shortened, connecting the bladder to the urethra results in a strained connection that can cause urinary incontinence post-prostatectomy.

SUMMARY

The present disclosure relates generally to supporting a connection of a bladder and urethra, for example, managing a shape of a junction between the bladder and the urethra to promote urinary continence after a prostatectomy.

In one or more cases, the disclosed technology relates to a device managing a shape of a junction between the bladder and the urethra. In one or more cases, the device comprises an implant having a first portion and a second portion forming a hollow interior area within the implant extending along a longitudinal axis thereof. In one or more cases, the first portion and the second portion each comprising a tubular shape centered about the longitudinal axis. In one or more cases, the first portion is configured to receive a portion of a urethra therein and to be attached thereto. In one or more cases, the second portion is configured to receive an extended portion of a bladder therein and to be attached thereto. In one or more cases, the implant is configured to encase a surgical connection of the urethra and the bladder in the hollow interior area of the implant and to support the operation of one or more sphincter muscles controlling the passage of liquid from the bladder to the urethra.

In one or more cases, the disclosed technology relates to a method of managing a shape of a junction between the bladder and the urethra to control the bladder. In one or more cases, the method comprises inserting a urethra through a hollow interior area of a device. In one or more cases, the hollow interior area extends along a longitudinal axis of the device. In one or more cases, the method includes attaching the urethra to the bladder. In one or more cases, the method includes attaching a first portion of the device to the urethra. In one or more cases, the first portion comprises a tubular shape centered about the longitudinal axis. In one or more cases, the method includes expanding the device longitudinally along the longitudinal axis to a deployed state in which a portion of the bladder extends into the second portion. In one or more cases, the method comprises attaching a second portion of the device to the bladder. In one or more cases, the second portion comprises a tubular shape centered about the longitudinal axis.

The foregoing and other objects, features, and advantages of the disclosure will be apparent from the following more particular descriptions of the embodiments as illustrated in the accompanying drawings.

BRIEF DESCRIPTION OF THE DRAWINGS

The following drawings are illustrative of particular embodiments of the present disclosure and therefore do not limit the scope of the present disclosure. The drawings are not to scale and are intended for use in conjunction with the explanations in the following detailed description.

FIG. 1A is a perspective view of an example support apparatus in a compressed state.

FIG. 1B is a perspective view of the example support apparatus in a partially expanded state.

FIG. 1C is a perspective view of the example support apparatus in a fully expanded state.

FIG. 2A illustrates the example support apparatus inserted over a sphincter muscle.

FIG. 2B illustrates a cross-sectional view of the example support apparatus attached to the one or more example sphincter muscles.

DETAILED DESCRIPTION

Figure 3A:
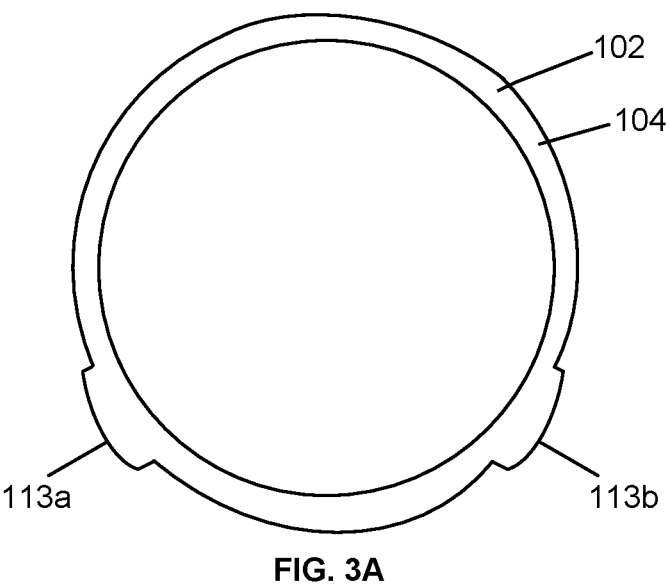
FIG. 3A is a top view of the example support apparatus, in which one or more example inflation balloons are in a deflated state.

The following discussion omits or only briefly describes conventional features of prostatectomies that are apparent to those skilled in the art. It is noted that various embodiments are described in detail with reference to the drawings, in which like reference numerals represent like parts and assemblies throughout the several views. Reference to various embodiments does not limit the scope of the claims attached hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest reasonable interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "includes" and/or "including," when used in this specification, specify the presence of stated features, elements, and/or components, but do not preclude the presence or addition of one or more other features, steps, operations, elements, components, and/or groups thereof. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively or operably connected" is such an attachment, coupling or connection that allows the pertinent structures to operate as intended by virtue of that relationship Embodiments of the present disclosure relate generally to supporting a connection of a bladder and urethra, for example, managing a shape of a junction between the bladder and the urethra to promote urinary continence after a prostatectomy. Such apparatus and methods may promote the normal operation of one or more sphincter muscles that control a bladder. Embodiments of support apparatus are described below with reference to FIGS. 1A-5B.

FIG. 1A is a perspective view of an example support apparatus 100 (hereinafter "apparatus 100"). FIG. 1B is a perspective view of the apparatus 100 in a partially expanded state. FIG. 1C is a perspective view of the apparatus 100 in a fully expanded state.

In one or more embodiments, the apparatus 100 includes an implant 102, one or more compressing members, such as compressing members 108a, 108b, 108c, 108d and compressing members 110a, 110b, 110c, and 110d, and one or more sizing members, such as sizing members 114a, 114b, and 114c. It is noted that FIGS. 1A, 1B, and 1C illustrate the apparatus 100 including the implant 102, compressing members 108a, 108b, 108c, 108d, compressing members 110a, 110b, 110c, and 110d, and sizing members 114a, 114b, and 114c. However, it should be understood that the apparatus 100 may include the implant 102 and none of the aforementioned members, or one or more of the aforementioned members. For example, the apparatus 100 may include the implant 102. In another example, the apparatus 100 may include the implant 102, compressing members 110a, 110b, 110c, and 110d, and sizing members 114a, 114b, and 114c. In yet another example, the apparatus 100 may include the implant 102, compressing members 108a, 108b, 108c, 108d, and compressing members 110a, 110b, 110c, and 110d.

The implant 102 may be a flexible tubular member having a first portion 104 and a second portion 106 forming a hollow interior area within the implant 102. The hollow interior area extends along a longitudinal axis L1 of the implant 102. In one or more cases, the first portion 104 of the implant 102 may be a flexible tubular member having a cylindrical body configured to receive at least a portion of a urethra. In one or more cases, the second portion 106 of the implant 102 may be a flexible tubular member configured to receive at least a portion of a sphincter muscle, such as, but not limited to, a bladder. In some cases, the second portion 106 may taper from a wider end 107 to a narrower end 109 proximal to the first portion 104. The first portion 104 and the second portion 106 may be integrally formed to have a unibody construction.

In one or more cases, the first portion 104 and the second portion 106 may be formed such that the entirety of the implant 102 has a tapered shape, in which a wider end of the implant (e.g., wider end 107 of the second portion 106) is formed on the bladder receiving end and a narrower end (e.g., the distal end 111 of the first portion 104) is formed on the urethra receiving end. In yet one or more other cases, the first portion 104 and second portion 106 may be formed such that the entirety of the implant 102 has a substantially cylindrical shape. In one or more cases, the implant 102 may preferably be formed of a compressible, shape-memory material, such as Nitinol or other types of polymers and biocompatible materials. In one or more cases, the material of implant 102 is compatible with antibiotics. Implant 102 may further comprise an antibacterial biomaterial, including, for example, an antibiotic coating. In one or more cases, the end 107 of the second portion 106 and/or the distal end 111 of the first portion 104 may include a flange that facilitates suturing the implant 102 to the bladder and urethra, respectively. The ordinary artisan will appreciate that end 107 and/or distal end 111 itself may not need to be sutured to the bladder or urethra, respectively, so long as the implant 102 is sufficiently anchored to the bladder and/or urethra.

When a portion of the bladder is inserted within the second portion 106, the portion of the bladder may be extended and narrowed within the second portion 106. In some cases the bladder may be further extended through the second portion 106 and into the first portion 104. The extended and narrowed portion of the bladder forms a pseudo-urethra and extends the effective length of urethra, thereby mitigating incontinence. In that way a longer effective length of urethra is provided by the actual urethra together with the portion of the bladder that is extended and narrowed to mimic a prostatic part of the urethra that was removed. That is, the implant 102 encases the surgical connection of the bladder and the urethra in the hollow interior area of the implant 102, and allows a portion of the bladder to function as urethra. The implant 102, meanwhile, mitigates the stress that an elongated and unconstrained bladder neck places on the sphincter muscle(s) that establish continence. Mitigating such stress using implant 102 may advantageously ameliorate or prevent urinary incontinence post prostatectomy.

In one or more cases, the implant 102 may be configured in a compressed state, as shown in FIG. 1A, and in various expanded states, as shown in FIGS. 1B and 1C. One or more compressing members may be removably disposed around the wall 105 of the implant 102, such that the implant 102 is retained in the compressed state until removal of the one or more compressing members. In one or more cases, a compressing member may be surgical thread made of material, such as silk or nylon, and capable of being tied together to compress at least a portion of the implant 102. In one or more other cases, the compressing member may be another type of compressing fastener such as a twist tie or zip tie.

In one or more cases, a compressing member, such as compressing member 108a, may advantageously facilitate installation of the implant into the body. By retaining the implant in a compressed state, the implant is physically smaller and more manageable during the initial insertion. Controlling the expansion of the implant thereafter beneficially allows for controlled suturing and shaping of the bladder and urethra. Such compressing member may extend along the inner surface of the wall through the hollow of the implant and along the outer surface of the wall 105 of the implant 102, in which the compressing member may be fastened to the implant 102 to compress at least a portion of the implant 102. In some cases, the compressing member may be retained around the entirety of the wall 105 to compress the respective portion of the implant 102. In other cases, the compressing member may be retained around a portion of the wall 105 to compress the respective portion of the implant 102. For example, the compressing members 108a, 108b, 108c, and 108d may be retained around the first portion 104 of the implant 102, thereby compressing the first portion 104 of the implant 102. In another example, compressing members 110a, 110b, 110c, and 110d may be retained around the second portion 106 of the implant 102, thereby compressing the second portion 106 of the implant 102.

By retaining compressing members around certain portions of the implant 102, compressing members may be selectively removed to expand certain portions of the implant 102. For instance, when compressing members 108a, 108b, 108c, and 108d are removed from implant 102, the first portion 104 of the implant 102 may be expanded along the longitudinal axis L1, as illustrated in FIG. 1B. In another instance, when compressing members 110a, 110b, 110c, and 110d are removed from the implant 102, the second portion 106 of the implant 102 may be expanded along the longitudinal axis L1, as illustrated in FIG. 1C. The sequence of removing the compressing members may be selected during installation to control how the implant expands relative to the points of attachment to the bladder or urethra. To deploy the implant 102 or a portion of the implant 102 into an expanded state, the compressing member 102 may be removed by, for example, cutting the compressing member or untying the compressing member. In one or more cases, the compressing members may include a visual identifier to signify the portion of the implant 102 being compressed by the compressing member. For example, the compressing members may be color coded such that each compressing member includes a different color. For instance, compressing members 108a, 108b, 108c, and 108d may be made of a surgical thread having a green color, and compressing members 110a, 110b, 110c, and 110d may be made of a surgical thread having a yellow color.

In one or more cases, the compressing members may be positioned to evenly retain the implant 102 in a compressed state. For example, when four compressing members are implemented, such as compressing members 110a, 110b, 110c, and 110d, the compressing members may be positioned at the 12 o'clock, 3 o'clock, 6 o'clock, and 9 o'clock positions of the implant 102 when viewed from a top view. It is noted that four compressing members are illustrated to compress the first portion 104 and the second portion 106, respectively. However, it should be understood that any number of compressing members may be used to retain the implant 102 in a compressed state. For example, two compressing members may be disposed around the entirety of the wall of the implant 102 at the 3 o'clock and 9 o'clock positions respectively to retain the implant 102 in a compressed state. In another example, two compressing members may be used to retain the first portion 104 in the compressed state, and three compressing members may be used to retain the second portion 106 in the compressed state. It is noted that the compressing members may be optionally included to compress the implant 102. That is, in the alternative to compressing one or more portions of the implant 102, the implant 102 may be initially configured in the expanded state as illustrated in FIG. 1C.

In one or more cases, the one or more sizing members 114a, 114b, and 114c may encircle portions of the wall 105 of the implant 102. In one or more cases, these components may form a zip tie or function as a zip tie. For example, sizing member 114c may encircle the second portion 106, and sizing members 114a and 114b may encircle opposite end portions of the first portion 104, as illustrated in FIG. 1C. In another example, one sizing member may encircle a portion of the wall 105 of the implant 102.

The sizing member, for example sizing member 114a, may be configured to increase and/or decrease the diameter of the wall 105 of the implant 102. By tightening the sizing member, the diameter of the wall 105 decreases, and by loosening the sizing member, the diameter of the wall 105 increases. For example, to decrease the diameter of the second portion 106, the sizing member 114c may be tightened. The sizing member may include a sizing strap, such as strap 116a, 116b, or 116c, and one or more sizing loops, such as sizing loops 118a, 118b, and 118c. The sizing loops may be circumferentially disposed around the outer surface of the wall 105 forming a guide for receiving the sizing strap. For example, the sizing strap 116b may encircle the wall 105 by passing through the sizing loops 118a. By inserting the sizing strap through the one or more sizing loops, the sizing loops 118a may maintain the position of the sizing strap on the wall 105 of the implant 102. In one or more cases, the sizing loop may be formed of the same material as the implant 102. In one or more other cases, the sizing loop may be formed of a surgical thread, in which opposite ends of the sizing loop are fastened to the wall 105, thereby forming a loop (e.g., a through-hole) under the unfastened portion of the sizing loop. The sizing strap may pass through the loop. In one or more cases, the sizing strap may be a zip tie, twist tie, surgical thread, or other like material that can be fastened around the wall 105 of the implant 102. In one or more cases, to size the sizing member, a user (such as but not limited to a physician surgically installing the implant 102) may insert a catheter into the patient and through the urethra, such that the catheter is positioned within the urethra or bladder and one or more of the sizing members. The user may tighten the sizing member until the user receives feedback that the sizing member is snugly fit around the urethra or bladder. For example, while tightening the sizing member, the user may feel increased tension as the diameter of the urethra or bladder is reduced around the catheter.

In one or more cases, the sizing member may include one or more burrs disposed on the sizing member and circumferentially disposed around the wall 105 of the implant 102. The burrs may protrude outward from the sizing member and may temporarily engage and anchor one or more surfaces of the bladder, urethra, or implant. The burrs may advantageously prevent, for example, the implant 102 from sliding along the urethra while the implant 102 is being attached to the urethra. In one or more cases, the sizing member may include loops or suture bands disposed on the sizing member and circumferentially disposed around the wall 105 of the implant 102. A user may pass sutures through the loops or suture bands to facilitate suturing the implant 102 to one or more portions of the urethra and bladder as described herein.

In one or more other cases, the implant 102 does not include a sizing member, but the diameter of the wall 105 is pre-sized to a diameter of a urethra, such that the implant may snugly receive at least a portion of the urethra therein. In yet one or more other cases, the implant 102 is pre-sized to a diameter of the urethra and includes one or more sizing members to make additional adjustments to the diameter of the implant 102.

Figure 3B:
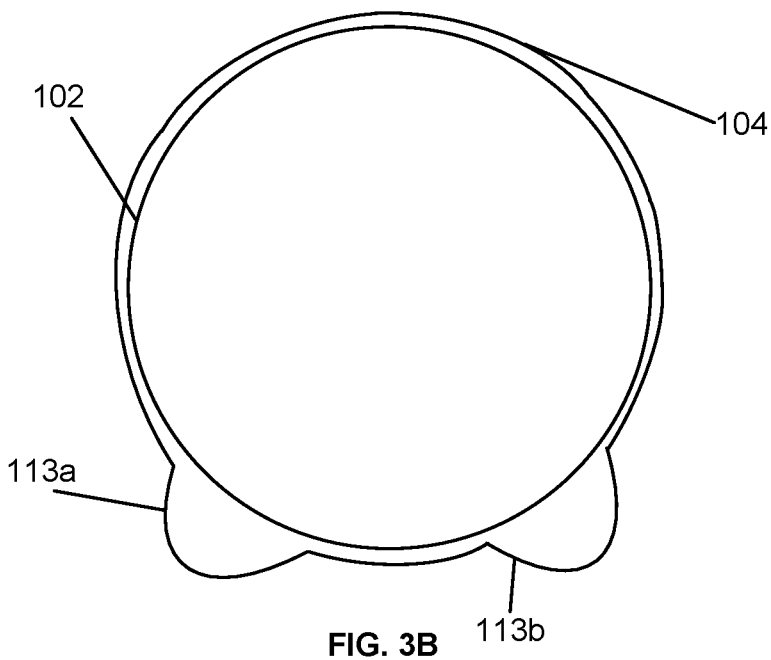
FIG. 3B is a top view of the example support apparatus, in which the one or more example inflation balloons are in an inflated state.

In one or more cases, one or more positioning members, such as positioning members 113a and 113b, may be pre-attached and disposed on an outer surface of the wall 105. The positioning members 113a and 113b each include a balloon, such as balloons 112a and 112b, and a valve, such as valve 120a and 120b. The positioning members 113a and 113b are configured to inflate by inserting a catheter into the respective valve 120a, 120b and inserting a solution, such as a saline solution, into the balloon. By inserting the saline solution into the balloon, the balloon may inflate outwards in a radial direction from the longitudinal axis L1, as illustrated in FIG. 3B. Conversely, by removing the saline solution from the balloon, the balloon may deflate inwards in the radial direction from the longitudinal axis L1, as illustrated in FIG. 3A. During the prostatectomy procedure, the implant 102 may be positioned such that when the balloons 112a and 112b are inflated post-prostatectomy, the balloons 112a and 112b may press against a portion of the patient's body causing the bladder neck to lift upwards as one or both of the balloons 112a and 112b are inflated. In one or more cases, all or a portion of the positioning member, such as the valve 120a of positioning member 113a, may be formed out of radio-opaque material or radiolucent material, such that the positioning member or a portion thereof may be visible in certain imaging procedures, such as, but not limited to a fluoroscopy. For example, using image guidance, such as viewing an x-ray, a user may guide the catheter to the radio-opaque or radiolucent valve 120a to inflate or deflate the balloon 112a. Although an embodiment having two positioning members 113a and 113b is shown, alternative numbers and layouts of positioning members would also be useful. For example, a single, larger member 113 could advantageously used. As a further example, multiple positioning members may be disposed around the perimeter of implant 102. Likewise, in other cases, implant 102 does not have a positioning member.

In one or more other cases, the one or more positioning members, such as positioning members 113a and 113b, may be coupled to the outer surface of the wall 105 after one or more portions of the implant 102 is configured in an expanded state. For instance, during the prostatectomy procedure, the first portion 104 is expanded and secured to at least a portion of the urethra; a user may position the positioning members 113a and 113b to the portion of the patient's body as described herein; and the user may couple the positioning members 113a and 113b to the outer surface of the wall 105. The user may couple the positioning members 113a and 113b to the wall 105 via adhesive, suturing, or other like coupling means. In yet one or more other cases, during a subsequent procedure (i.e., post-prostatectomy), a user may position and couple the positioning members 113a and 113b to the outer surface of the wall 105 as described herein. Moreover, during the post-prostatectomy procedure, the user may inflate the positioning members 113a and 113b as described herein.

During a prostatectomy, a user may remove all or a portion of the prostate gland. Having removed all or a portion of the prostate gland, the user inserts a detached urethra 200 through the apparatus 100, which is configured in the compressed state. The user may suture an end portion 206 of the bladder 202 to an end portion 208 of the urethra 200, via, for example, a surgical suture 204, as illustrated in FIG. 2A. In one or more cases, having attached the urethra 200 and the bladder 202, the apparatus 100 may be attached to the urethra 200 and the bladder 202 in a variety of steps and in various locations of the urethra 200 and the bladder 202.

For instance, the user may remove one or more compressing members, such as compressing members 108a, 108b, 108c, and 108d, to expand the first portion 104 of the apparatus 100 in a direction of the longitudinal axis L1. For the cases in which the apparatus 100 includes pre-attached positioning members 113a and 113b, the user may position the positioning members 113a and 113b to be inflated against a body post-prostatectomy, as discussed herein. The user may then suture the distal end 210 of the first portion 104 at various points, such as point 212, around the urethra 200, thereby securing the position of the positioning members. In some cases, the user may suture the distal end 210 of the first portion 104 on or as close to pelvic floor as possible. It is noted that the user may also remove the compressing members 108a, 108b, 108c, and 108d after suturing the distal end 210 of the apparatus 100 to the urethra 200. In some cases, the user may set the diameter of the wall 105 via the one or more sizing members 114a and 114b as discussed herein, thereby setting the diameter of the urethra 200. The user may suture the proximal end 216 of the first portion 104 at various points, such as points 214, on the end portion 208 of the urethra 200. The user may then remove compressing members 110a, 110b, 110c, and 110d to expand the second portion 106 in the direction of the longitudinal axis L1. It is noted that the second portion 106 may be expanded before positioning the positioning members 113a and 113b; before suturing the distal end 210 of the first portion 104 to the urethra 200; before setting the diameter of the wall 105; or before suturing the proximal end 216 of the first portion 104 to the end portion 208 of the urethra 200.

Having sutured the proximal end 216 of the first portion 104 to the end portion 208 of the urethra 200, the user may suture a proximal end portion 220 of the bladder 202 to the second portion 106 at various suture points, such as suture points 218. When suturing the proximal end portion 220 to the second portion 106, the proximal end portion 220 of the bladder 202 may extend into and narrow within the second portion 106. Further, the user may set the diameter of the wall 105 of the second portion 106 to further narrow the proximal end portion 220 within the second portion 106. The apparatus 100 extends the effective length of the urethra 200 via the extended and narrowed portion of the bladder, as such, incontinence after the prostatectomy is mitigated or reduced. For the cases in which the positioning members 113a and 113b are not pre-attached, the positioning members 113a and 113b may positioned and coupled to the wall 105 after expanding the first portion 104, after expanding the second portion 106, or after suturing the proximal end portion 220 to the second portion 106. The positioning members 113a and 113b may be positioned in a deflated stated.

It is noted that the procedure described herein discusses removing the compressing members to expand the implant 102. However, for cases in which the implant 102 does not include the compressing members and the implant 102 is initially configured in the expanded state, the user inserts a detached urethra 200 through the apparatus 100, attaches the urethra 200 and the bladder 202 as described herein, and attaches the portions of the apparatus 100 to the respective portions of the urethra 200 and bladder 202 as described herein.

For some cases in which the patient fails to regain continence or begins to develop symptoms of incontinence post-prostatectomy and the device is fitted with positioning members 113a and 113b, in a subsequent procedure, the user may make adjustments to urethral positioning by inserting a catheter into the patient, and guiding the catheter to the one or more positioning members 113a and 113b, as described herein. The user may insert the catheter into the valves 120a and 120b and inflate the balloons 112a and 112b. As the balloons 112a and 112b are inflated, the balloons contact and press against a portion of the patient, thereby causing the apparatus 100 and the bladder neck to lift upwards and reestablish continence. In addition to or as an alternative to inflating the balloons 112a and 112b, the user may tighten one or more of the sizing members 114a, 114b, and 114c. For the cases in which the positioning members 113a and 113b were not coupled to the implant 102 during the prostatectomy procedure, during a subsequent procedure, the user may invasively position and couple the positioning members 113a and 113b to the outer surface of the wall 105 as described herein. Having coupled the positioning members to the implant 102, the user may inflate the balloons 112 and 112b as described herein.

In one or more other cases in which all or a portion of the prostate gland is removed, the user may alternatively insert the detached urethra 200 through the apparatus 100, which is configured in the compressed state. The user may suture the distal end 210 of the first portion 104 to the urethra 200, and suture the end portion 206 of the bladder 202 to the end portion 208 of the urethra 200. The user may subsequently attach the remaining portions of the apparatus 100 as described herein.

For other cases in which most or all of the urethra 200 is removed during the prostatectomy, the user may suture the distal end 210 of the first portion 104 on or close to the pelvic floor, expand and position the apparatus 100 as described herein, and suture the proximal end portion 220 to the second portion 106 as described herein. In such cases, as the urethra 200 is not long enough to attach the proximal end 216 of the first portion 104, the user may preferably not suture the proximal end 216 of the first portion 104.

Figure 4:
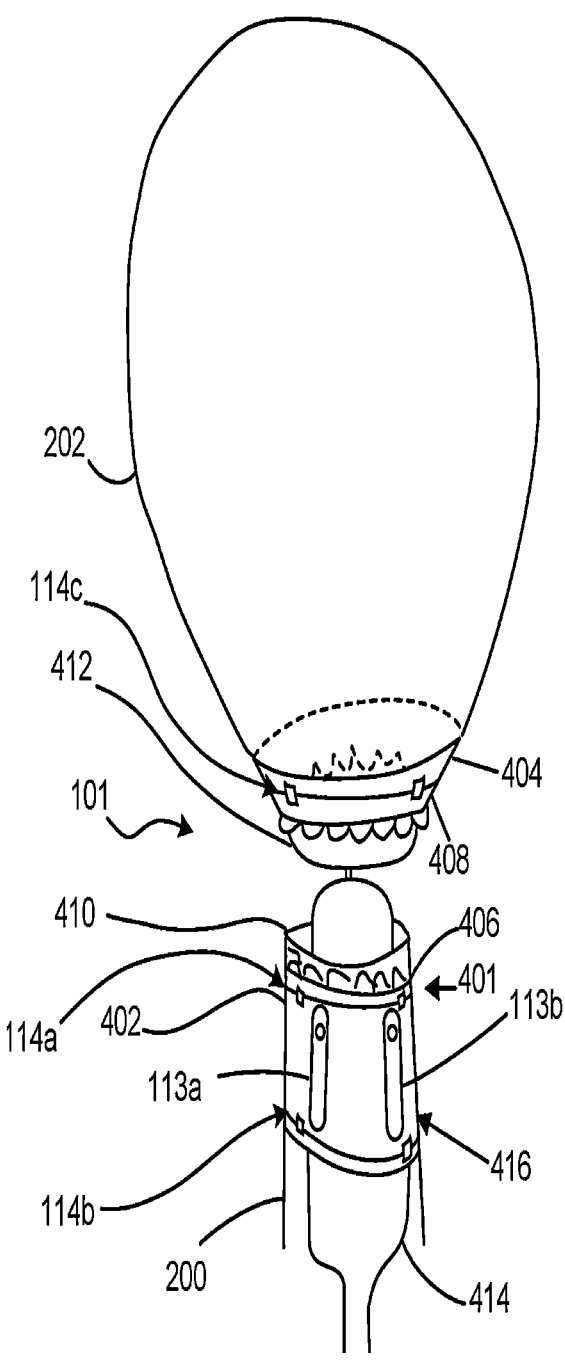
FIG. 4 is a perspective view of another example support apparatus.

FIG. 4 is a perspective view of another example support apparatus 101 (hereinafter "apparatus 101").

In one or more embodiments, the apparatus 101 includes an implant 401 having a first portion 402 and a second portion 404, one or more sizing members, such as sizing members 114a, 114b, and 114c, and one or more positioning members, such as positioning members 113a and 113b. It is noted that the sizing members 114a, 114b, and 114c and the positioning members 113a and 113b of apparatus 101 include the same or similar features as the sizing members 114a, 114b, and 114c and the positioning members 113a and 113b of apparatus 100, as such the description of these members is not repeated.

In one or more cases, the first portion 402 is a cylindrically tubular member that includes a flange 406 on the proximal end of the first portion 402, and the second portion 404 is a tubular member having a funnel-like shape that includes a flange 408 on a proximal end of the second portion 404. The flanges 406 and 408 are formed of a rigid or semi-rigid material that facilitate suturing together the first portion 402 and the second portion 404.

During a prostatectomy, the user may remove all or a portion of the prostate gland. Having removed all or a portion of the prostate gland, the user inserts a detached urethra 200 through the first portion 402. In one or more cases, the first portion 402 may be configured in a compressed state via one or more compressing members, such as compressing members 108a, 108b, 108c, and 108d. In some cases, the user may remove the compressing members after suturing a distal end portion 416 of the first portion 402 to the urethra 200. In other cases, the user may remove the compressing members before suturing a distal end portion 416 of the first portion 402 to the urethra 200. The user may suture the distal end portion 416 of the first portion 402 to the urethra 200 such that a portion of the proximal end 410 of the urethra 200 extends beyond the proximal end 406 of the first portion 402. The user may insert a catheter 414 through the urethra 200 and position the catheter 414 within the first portion 402, such that the shape of the urethra 200 is maintained or substantially maintained when attaching the bladder 202 to the urethra 200.

The user may insert the second portion 404 over the proximal end 412 of the bladder 202, and suture the second portion 404 to the bladder 202 such that a portion of the proximal end 412 of the bladder 202 extends beyond the proximal end 408 of the second portion 404. The user may attach the bladder 202 to the urethra 200 by suturing the portions of the bladder 202 and the urethra, which extend beyond the proximal ends 406 and 408 respectively, to one another. Having attached the bladder 202 and the urethra 200, the user may further extend the proximal end 406 of the first portion 402 and/or the proximal end 408 of the second portion 404 towards one another. The user may then suture the first portion 402 and the second portion 404 to one another. Subsequently, the user may remove the catheter 414. In a same or similar manner as the apparatus 100, the apparatus 101 extends the effective length of the urethra 200 via the extended and narrowed portion of the bladder, and as such, incontinence after the prostatectomy may be further mitigated or reduced.

Figure 5A:
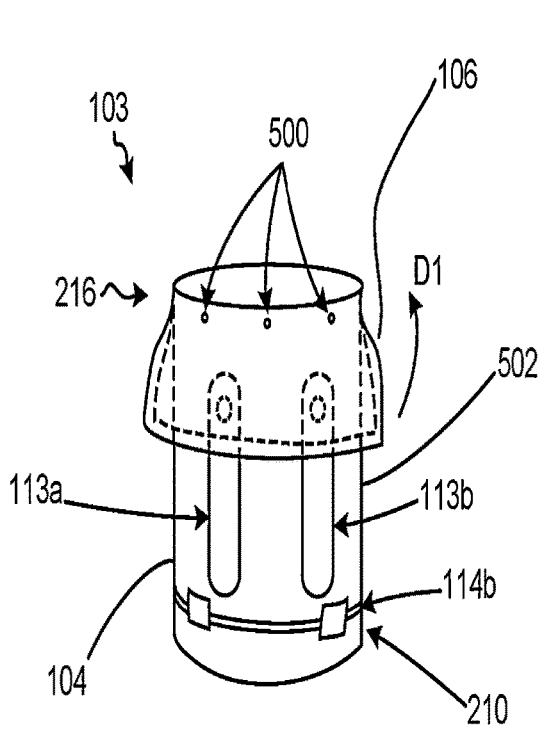
FIG. 5A is a perspective view of another example support apparatus in a folded state.
Figure 5B:
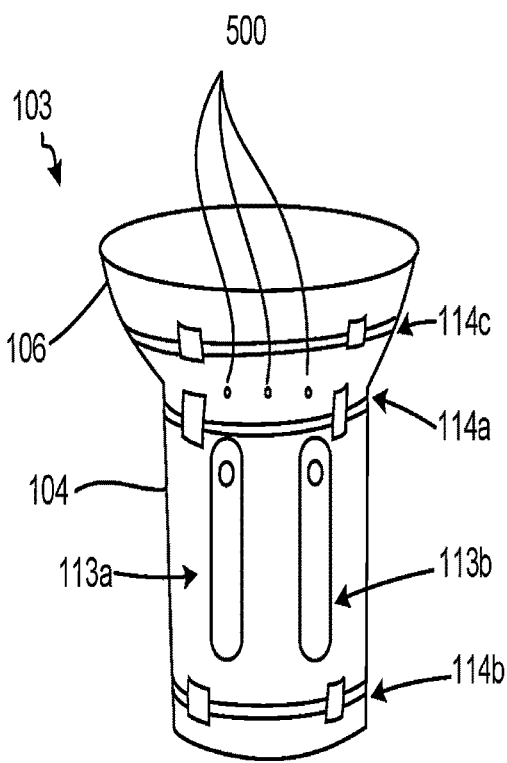
FIG. 5B is a perspective view of the example support apparatus of FIG. 5A in an unfolded state.

FIG. 5A is a perspective view of another example support apparatus 103 (hereinafter "apparatus 103") in a folded state. FIG. 5B is a perspective view of the apparatus 103 in an unfolded state.

In one or more embodiments, the apparatus 103 includes an implant 502, one or more sizing members, such as sizing members 114a, 114b, and 114c, and one or more positioning members, such as positioning members 113a and 113b. It is noted that the sizing members 114a, 114b, and 114c and the positioning members 113a and 113b of apparatus 103 include the same or similar features as the sizing members 114a, 114b, and 114c and the positioning members 113a and 113b of apparatus 100, as such the description of these members is not repeated. Further, one or more compressing members, such as compressing members 108a, 108b, 108c, and 108d, may be removably disposed around at least a portion of the first portion 104. The one or more compressing members may retain the first portion 104 in a partially compressed state such that a portion of the first portion 104 is not covered by the folded second portion 106 and can be sutured to the urethra 202.

In one or more cases, the implant 502 includes the first portion 104 and the second portion 106. It is noted that the first portion 104 and the second portion 106 of implant 502 include the same or similar features as the first portion 104 and the second portion 106 of implant 102, as such a description of these features is not repeated. The implant 502 is distinguishable from implant 102 in that the implant 502 is initially configured in a folded state, as illustrated in FIG. 5A. In one or more cases, the second portion 106 is folded outwards and over at least a portion of the first portion 104 in the folded state.

During a prostatectomy, the user may remove all or a portion of the prostate gland. Having removed all or a portion of the prostate gland, the user inserts a detached urethra 200 through the first portion 104 and folded second portion 106 of the implant 503. In some cases, the user may suture the distal end 210 of the first portion 104 to the urethra 200, and, before or after suturing the distal end 210 to the urethra 200, the user may suture the proximal end 216 of the first portion 104 from the inside of the implant 502 to the urethra 200 at one or more suture points, such as suture points 500. The user may suture the bladder 202 to the urethra 200 as described herein. It is noted that the user may suture the bladder 202 to the urethra 200 before suturing the distal end 210 of the first portion 104 to the urethra 200 and suturing the proximal end 216 to the urethra 200; in between suturing the distal end 210 of the first portion 104 to the urethra 200 and suturing the proximal end 216 to the urethra 200; or after suturing the distal end 210 of the first portion 104 to the urethra 200 and suturing the proximal end 216 to the urethra 200. Subsequent to suturing the first portion 104 to the urethra 200 and suturing the bladder 202 and the urethra 200, the user may unfold the second portion 106 in a direction D1 into the unfolded state as shown in FIG. 5B. The user may suture the second portion 106 to the bladder 202 as described herein.

It is noted that the user may perform the procedures described herein manually or robot-assisted, such as with a robotic surgical system like the Da Vinci™ surgical system. It should also be understood that although three suture points are illustrated for suturing a portion of the implant 102 to respective portions of the urethra and bladder, it should be understood that any number of sutures and suture points may be used to fasten the implant to the urethra and bladder. Moreover, the embodiments discussed herein are directed to prostatectomy procedures; however, it should be understood that the apparatus and methods described herein may be applicable to other procedures that involve surgically connecting body parts, such as veins or arteries to respective organs.

The various embodiments described above are provided by way of illustration only and should not be construed to limit the claims attached hereto. Those skilled in the art will readily recognize various modifications and changes that may be made without following the example embodiments and applications illustrated and described herein, and without departing from the spirit and scope of the following claims.

What is claimed is:

1. A device for mitigating urinary incontinence post prostatectomy, the device comprising:

an implant having a first portion and a second portion, wherein the first and second portions are configured to form a hollow interior area within the implant extending along a longitudinal axis thereof, wherein:

the first portion and the second portion are each configured to form a tubular shaped wall centered about the longitudinal axis, the first portion is configured to receive a portion of a urethra therein, the second portion is configured to receive an extended portion of a bladder therein, and the implant is configured to encase the portion of the urethra and the extended portion of the bladder in the hollow interior area of the implant; and wherein the device is further configured:

to lengthen the extended portion of the bladder along the longitudinal axis by extending and narrowing the extended portion of the bladder within the hollow interior area of the device to increase effective urethral length sufficient to mitigate stress that the bladder places on one or more sphincter muscles controlling passage of liquid from the bladder to the urethra to thereby mitigate incontinence.

2. The device of claim 1, wherein the second portion has a tapered shape about the longitudinal axis that tapers outward from a first end of the second portion to a second end of the second portion, the second end being wider than the first end.

3. The device of claim 1, wherein the device is configured to extend and narrow the extended portion of the bladder through the second portion of the implant and into the first portion of the implant, further increasing effective urethral length.

4. The device of claim 1, wherein the implant is compressible and configured to expand in a direction of the longitudinal axis from a compressed state to a deployed state.

5. The device of claim 4, wherein the implant is configured to be retained in the compressed state by one or more compressing members.

6. The device of claim 5, wherein the one or more compressing members comprise a first compressing member and a second compressing member; wherein:

the first compressing member is removably disposed around at least a portion of the tubular shaped wall of the first portion such that at least part of the first portion is retained in the compressed state until removal of the first compressing member, and the second compressing member is removably disposed around at least a portion of the tubular shaped wall of the second portion such that at least part of the second portion is retained in the compressed state until removal of the second compressing member.

7. The device of claim 1, wherein the first portion has a distal end that is distal from the second portion, and wherein the distal end is configured to be sutured on or close to a pelvic floor associated with the urethra.

8. The device of claim 1, wherein the implant comprises one or more loops that facilitate attaching the implant to one or more of the bladder, the urethra, and a pelvic floor.

9. The device of claim 1, wherein the implant comprises a memory shape material.

10. The device of claim 1, wherein the first portion and the second portion are removably coupled to one another.

11. The device of claim 1, wherein the implant has a substantially cylindrical shape.

12. The device of claim 1, wherein the implant comprises a tapered shape about the longitudinal axis that tapers outward from a first end of the implant to a second end of the implant, the second end being wider than the first end.

13. The device of claim 1, wherein the implant further comprises an antibacterial biomaterial.

14. The device of claim 1, wherein the implant is formed of a surgical thread.

15. The device of claim 1, further comprising a flange configured to secure the implant to the urethra or the extended portion of the bladder.

16. The device of claim 1, wherein the tubular shaped wall includes an inner surface and an outer surface, forming an encasement.

17. The device of claim 1, wherein the first portion and the second portion are integrally formed to have a unibody construction-continuous and non permeable.

18. A device for mitigating urinary incontinence post prostatectomy, the device comprising:

a compressible implant configured to expand and compress along a longitudinal axis between a compressed state and an expanded state, the compressible implant having a first portion and a second portion that extend along, and are centered about, the longitudinal axis, the compressible implant forming a hollow interior area within the compressible implant that is centered about the longitudinal axis, wherein the first portion and the second portion are each configured to form a tubular shaped wall centered about the longitudinal axis; and wherein the compressible implant is configured to increase an effective urethral length by extending and narrowing an extended portion of a bladder along the longitudinal axis while constraining the extended portion of the bladder within the hollow interior area of the compressible implant to mitigate stress that the bladder places on one or more sphincter muscles controlling passage of liquid from the bladder to a urethra surgically attached to the bladder to thereby mitigate incontinence.

19. The device of claim 18, wherein the compressible implant comprises loops that facilitate securing the compressible implant to one or more of the bladder, the urethra, and a pelvic floor.

20. The device of claim 18, wherein when the compressible implant is in the expanded state, the second portion has a tapered shape about the longitudinal axis that tapers outward from a first end of the second portion to a second end of the second portion, the second end being wider than the first end.

21. The device of claim 18, wherein the compressible implant is configured to be retained in the compressed state along the longitudinal axis by one or more compressing members.

22. A device for mitigating urinary incontinence post prostatectomy, the device comprising:

an implant having a first portion and a second portion, wherein the first and second portions are configured to form a hollow interior area within the implant extending along a longitudinal axis thereof, wherein:

the first portion and the second portion are each configured to form a tubular shaped wall centered about the longitudinal axis, the second portion extending between a proximal end of the second portion and a distal end of the second portion, wherein the proximal end is proximal to the first portion and has a width that is the same as a width of the first portion, and the distal end is distal from the first portion and has a width that is wider than the width of the first portion; and wherein the implant is configured to lengthen an extended portion of a bladder along the longitudinal axis by extending and narrowing the extended portion of the bladder while constraining the extended portion of the bladder within the hollow interior area of the implant to mitigate stress that the bladder places on one or more sphincter muscles controlling passage of liquid from the bladder to a urethra surgically attached to the bladder to thereby mitigate incontinence.

23. The device of claim 22, wherein the implant comprises loops that facilitate securing the implant to one or more of the bladder, the urethra, and a pelvic floor.

24. The device of claim 22, wherein the implant is configured to expand and compress along the longitudinal axis between a compressed state and an expanded state.

25. The device of claim 24, wherein the implant is configured to be retained in the compressed state by one or more compressing members.

* * * * *